United States Patent [19]

Žmitek et al.

[11] Patent Number: 4,952,565
[45] Date of Patent: Aug. 28, 1990

[54] INCLUSION COMPLEX OF IBUPROXAM WITH BETA-CYCLODEXTRIN, A PROCESS FOR PREPARING THE SAME AND A PHARMACEUTICAL PREPARATION CONTAINING THE SAME

[76] Inventors: Janko Žmitek, Poklukarjeva 6; Jenny Milovac, Gotska 13, both of YU-61000 Ljubljana; Zdravko Kopitar, Muljava 7, YU-61234 Mengeš; Mirjan Žorž, Prešernova 53, YU-61290 Grosuplje; Boris Rusjakovski, Linhartova 96, YU-61000 Ljubljana, all of Yugoslavia

[21] Appl. No.: 119,933

[22] Filed: Nov. 13, 1987

[30] Foreign Application Priority Data

Nov. 13, 1986 [YU] Yugoslavia .................. 1932/86

[51] Int. Cl.$^5$ .................. A61K 31/00; C08B 37/00
[52] U.S. Cl. .................. 514/58; 536/46; 536/103; 514/532; 514/965; 514/777
[58] Field of Search .................. 260/500.5 H; 536/124, 536/46, 103; 514/58, 532, 965, 777

[56] References Cited

U.S. PATENT DOCUMENTS

| | | | |
|---|---|---|---|
| 4,061,668 | 12/1977 | Orzalesi et al. | 260/500.5 H |
| 4,082,707 | 4/1978 | Orzalesi et al. | 514/916 |
| 4,565,807 | 1/1986 | Vekama et al. | 514/58 |
| 4,603,123 | 7/1986 | Chiesi et al. | 514/58 |
| 4,834,985 | 5/1989 | Elger et al. | 424/488 |

FOREIGN PATENT DOCUMENTS 55-092341  1/1979  Japan .................. 514/58

OTHER PUBLICATIONS

Charaterization, Dissolution and Bioavailability in Rats of Ibuprofen-β-Cyclodextrin Complex System by DahNan D. Chow and Adel H. Karara, International Journal of Pharmaceutics, 28 (1986), 95–101.

Primary Examiner—Ronald W. Griffin
Assistant Examiner—Everett White
Attorney, Agent, or Firm—Pollock, Vande Sande & Priddy

[57] ABSTRACT

A new inclusion complex of ibuproxam with beta-cyclodextrin is described, which is prepared by adding ibuproxam to a boiling aqueous solution of beta-cyclodextrin, stirring the reaction mixture at the boiling temperature, cooling to a temperature of 0° C. to 5° C. and isolating the title complex.

The analgesic, antipyretic and antiinflammatory properties of the inclusion complex of ibuproxam with beta-cyclodextrin are equivalent to those of ibuproxam alone, but owing to its better water-solubility the complex can be more easily formulated into pharmaceutical forms.

4 Claims, 9 Drawing Sheets

DISSOLUTION RATES OF IBUPROXAM AND OF ITS INCLUSION COMPLEX WITH BETA-CYCLODEXTRIN IN ARTIFICIAL GASTRIC AND INTESTINAL JUICES

—□— inclusion complex of ibuproxam with beta-cyclodextrin
—△— ibuproxam
—○— physical mixture of ibuproxam and beta-cyclodextrin

FIG. 4

DISSOLUTION PROFILES OF IBUPROXAM IN ARTIFICIAL
GASTROINTESTINAL JUICE IN FUNCTION OF TIME

— o — ibuproxam powder, 400 mg

— △ — inclusion complex of ibuproxam with beta-cyclodextrin, 2.87 g (equiv. to 400 mg ibuproxam)

— — — — solution (average of 3 tests)

FIG. 5

EFFECT OF THE DISSOLUTION RATE OF IBUPROXAM
ON THE ABSORPTION RATE

—o— ibuproxam powder, 400 mg

—△— inclusion complex of ibuproxam with beta-cyclodextrin,
2.87 g (equiv. to 400 mg ibuproxam)

—  —  — solution

FIG. 6

CONCENTRATIONS OF IBUPROFEN IN PLASMA AFTER APPLICATION OF IBUDROS[R] TABLETS (●) AND INCLUSION COMPLEX OF IBUPROXAM WITH BETA-CYCLODEXTRIN (■) TO 9 BEAGLE DOGS

INCLUSION COMPLEX OF IBUPROXAM WITH BETA-CYCLODEXTRIN, A PROCESS FOR PREPARING THE SAME AND A PHARMACEUTICAL PREPARATION CONTAINING THE SAME

TECHNICAL FIELD OF THE INVENTION

The invention belongs to the field of pharmaceutical industry and relates to a novel inclusion complex of ibuproxam with beta-cyclodextrin, to a process for preparing the same and to a pharmaceutical preparation containing the same.

Ibuproxam is a valuable substance having analgesic, antipyretic and anti-inflammatory properties, which, owing to the conversion to the title complex, becomes better water-soluble.

TECHNICAL PROBLEM

There exists a constant need for the conversion of ibuproxam, which is poorly water-soluble, to a form having improved aqueous solubility, which would make possible the formulation of a pharmaceutical preparation, from which ibuproxam would dissolve quickly and completely, thereby also increasing the rate and extent of its resorption from the gastro-intestinal tract and at the same time reducing its toxicity.

PRIOR ART

Ibuproxam is the generic name for 2-(4-isobutyl-phenyl)-propiohydroxamic acid of the formula which was disclosed for the first time in DE patent No. 24 00 531 as a substance with valuable analgesic, antipyretic and anti-inflammatory properties. Ibuproxam is a white crystalline substance, which is poorly water-soluble.

There are well-known difficulties encountered when preparing pharmaceutical formulations from therapeutically active substances having poor aqueous solubility as well as other problems, e.g. dissolution difficulties, i.e. a poor rate of release and hence a poor or variable bioavailability.

To overcome these difficulties, complexing with cyclodextrins has been employed, particularly with substances having very low aqueous solubility, though the complexes are not always efficient.

The inclusion complexes of different compounds with cyclodextrins are known from ample literature sources, such as J. Szejtli, Cyclodextrins and their Inclusion Complexes, Akademiai Kaido, Budapest 1982. Cyclodextrins are cyclic compounds consisting of 6, 7 or 8 glucopyranose units, linked together by alpha-1,4-glucosidic bonds. They are characterized by a cylindric structure and a special arrangement of hydroxyl groups, whereby the outer surface of the ring formed by cyclodextrin is hydrophilic, ensuring water-solubility, whilst the inner surface is lipophilic, permitting other molecules, known as "guest molecules", or parts thereof which are less polar than water (hydrophobic molecules) and are of suitable dimension, to penetrate the lipophilic cavity of the inner part of the cylindric cyclodextrin molecule, forming thereby the inclusion complex.

DESCRIPTION OF THE SOLUTION OF THE TECHNICAL PROBLEM WITH WORKING EXAMPLES

The object of the present invention is to convert ibuproxam to a form having an increased aqueous solubility, which would make it possible to produce pharmaceutical preparations with improved bioavailability.

This object can be achieved by bonding ibuproxam into the structure of the cyclodextrin molecule, whereby a new inclusion complex having an increased aqueous solubility is formed as a white powder.

From among different cyclodextrins there can be used alpha-cyclodextrin, beta-cyclodextrin and gamma-cyclodextrin, preferably beta-cyclodextrin. The complex may be prepared by methods known for the preparation of inclusion complexes of cyclodextrins. To this end ibuproxam is reacted with a boiling aqueous solution of beta-cyclodextrin, the reaction mixture is cooled and the resulting complex is isolated.

Ibuproxam and beta-cyclodextrin are reacted in a molar ratio of 1:1 to yield a complex containing about 14% of ibuproxam.

The resulting complex provides for a more convenient way of administering ibuproxam, the cyclodextrin acting merely as a solubilizing agent and not altering the therapeutic behavior of the active substance in any way.

The invention also relates to pharmaceutical formulations, comprising a therapeutically active amount of an inclusion complex of ibuproxam with beta-cyclodextrin together with a pharmaceutically acceptable carrier therefor and other usual excipients.

The pharmaceutical preparations may be conveniently in dosage unit form. The dose to be administered will depend on various factors, such as the state and the age of the patient, the route of administration and the like. Suitable forms of pharmaceutical formulations include tablets, capsules, and syrups. These formulations, in addition to the active substance, include diluents, such as lactose, dextrose and the like, lubricating agents, such as talcum, stearic acid and salts thereof, polyethyleneglycol, binders, fillers, dyes and the like.

The formulation may be prepared according to known methods, such as mixing, granulating, dissolving etc.

The invention is illustrated in more detail in the following Examples, which are not intended to be a limitation thereof.

EXAMPLE 1

Preparation of an inclusion complex of ibuproxam with beta-cyclodextrin

Beta-cyclodextrin (240 g, 0.2 moles) and water (760 ml) are heated to the boiling point, ibuproxam (44.2 g, 0.2 moles) is added to this boiling solution and the solution is vigorously stirred for 2 minutes. Ibuproxam that was not dissolved (about 2 g) is filtered off and the filtrate is cooled to 0° to 5° C. under stirring. The complex which separates is sucked off and dried in vacuo at about 50° C. Thus, there are obtained 275 g of the inclusion complex of ibuproxam with beta-cyclodextrin in the form of a white powder.

The complex contained 14.1% of ibuproxam as shown by spectrophotometric determination.

EXAMPLE 2

Preparation of an inclusion complex of ibuproxam with beta-cyclodextrin

Beta-cyclodextrin (1135 g, 1 mole) is dissolved in water (10 l) at about 70° C. and the solution is heated to boiling. Ibuproxam (221 g, 1 mole) is added to the boiling solution. After the dissolution of ibuproxam the hot solution is filtered if necessary and cooled to 0° to 5° C. under stirring. The complex is sucked off and dried in vacuo at about 50° C. Thus, there are obtained 950 g of the title complex in the form of a white powder. The filtrate is evaporated in vacuo to ⅓ of the original volume and cooled to 0° to 5° C. The precipitate is sucked off and dried in vacuo at about 50° C. Thus, there are obtained another 340 g of the complex.

The complex contained 13.9% of ibuproxam as shown by spectrophotometric determination.

EXAMPLE 3

Solubility in water

Comparative solubility of ibuproxam alone and of its inclusion complex with beta-cyclodextrin The concentrations of the dissolved ibuproxam at room temperature were determined in clear filtrates of the saturated solutions by liquid chromatography using the external standard method.

|  | non-complexed | complexed |
|---|---|---|
| ibuproxam | 11 mg/100 ml | 256 mg/100 ml |

EXAMPLE 4

Differential scanning calorimetry

Figure 1A:
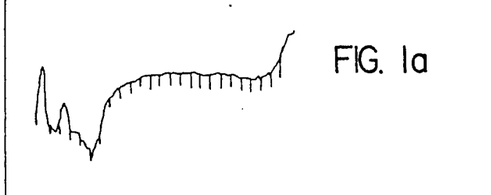
Figures 1B, 1C:
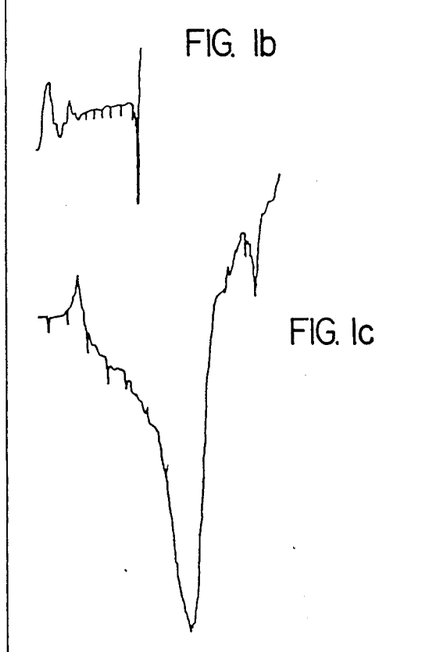
Figure 1D:
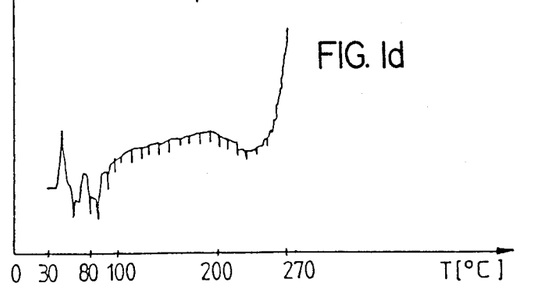
Figure 2A:
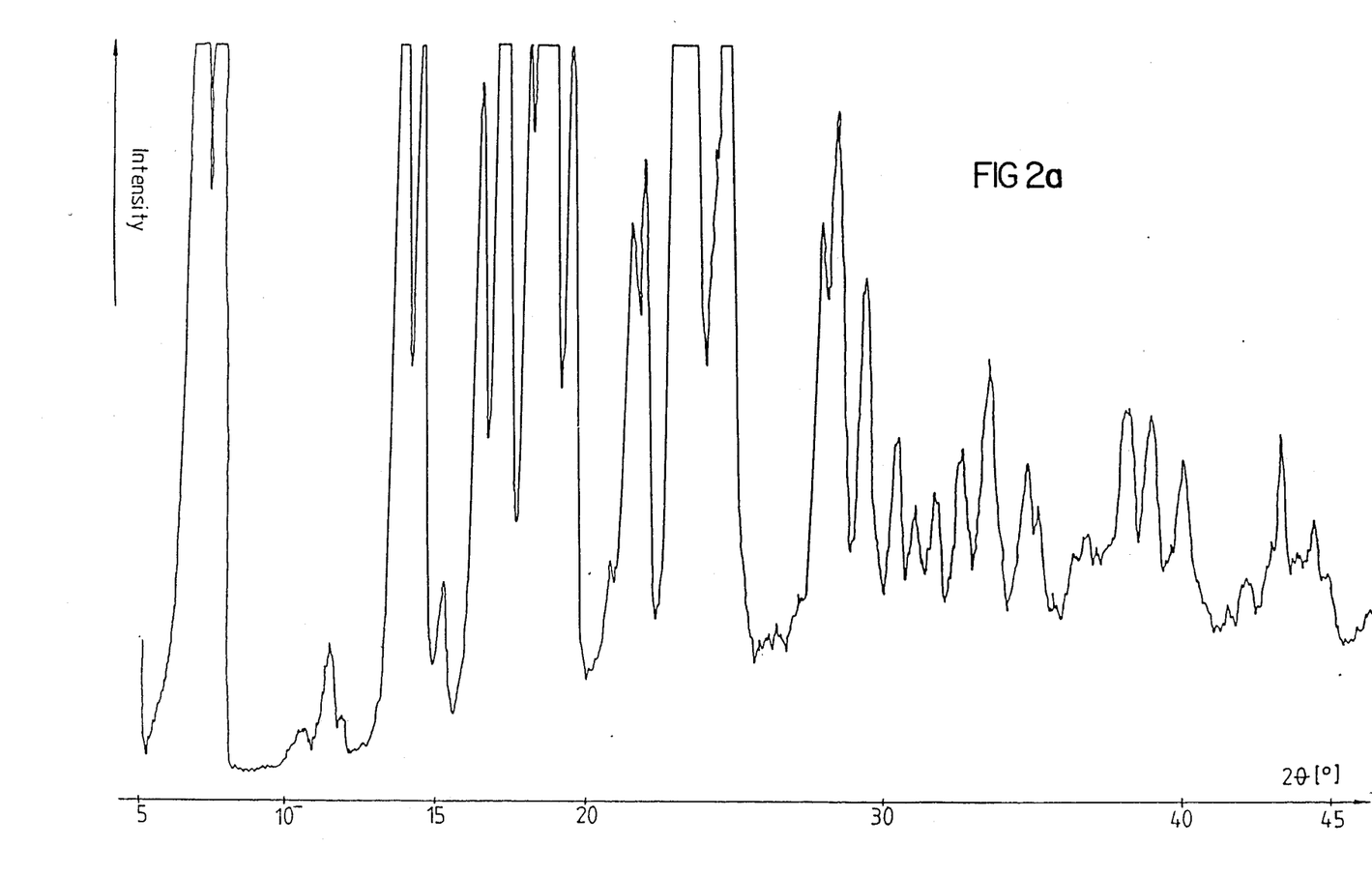
Figure 2B:
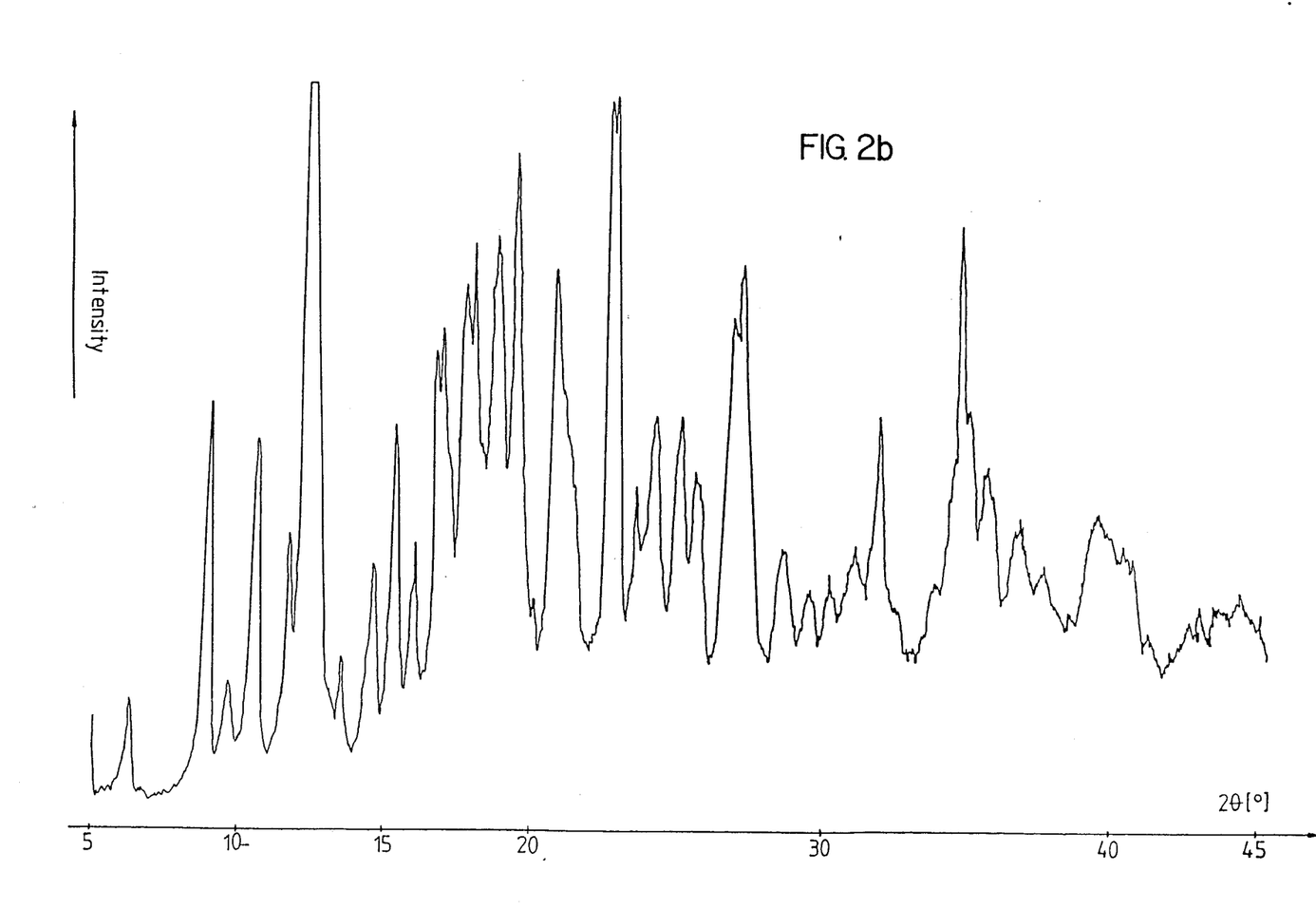
Figure 2C:
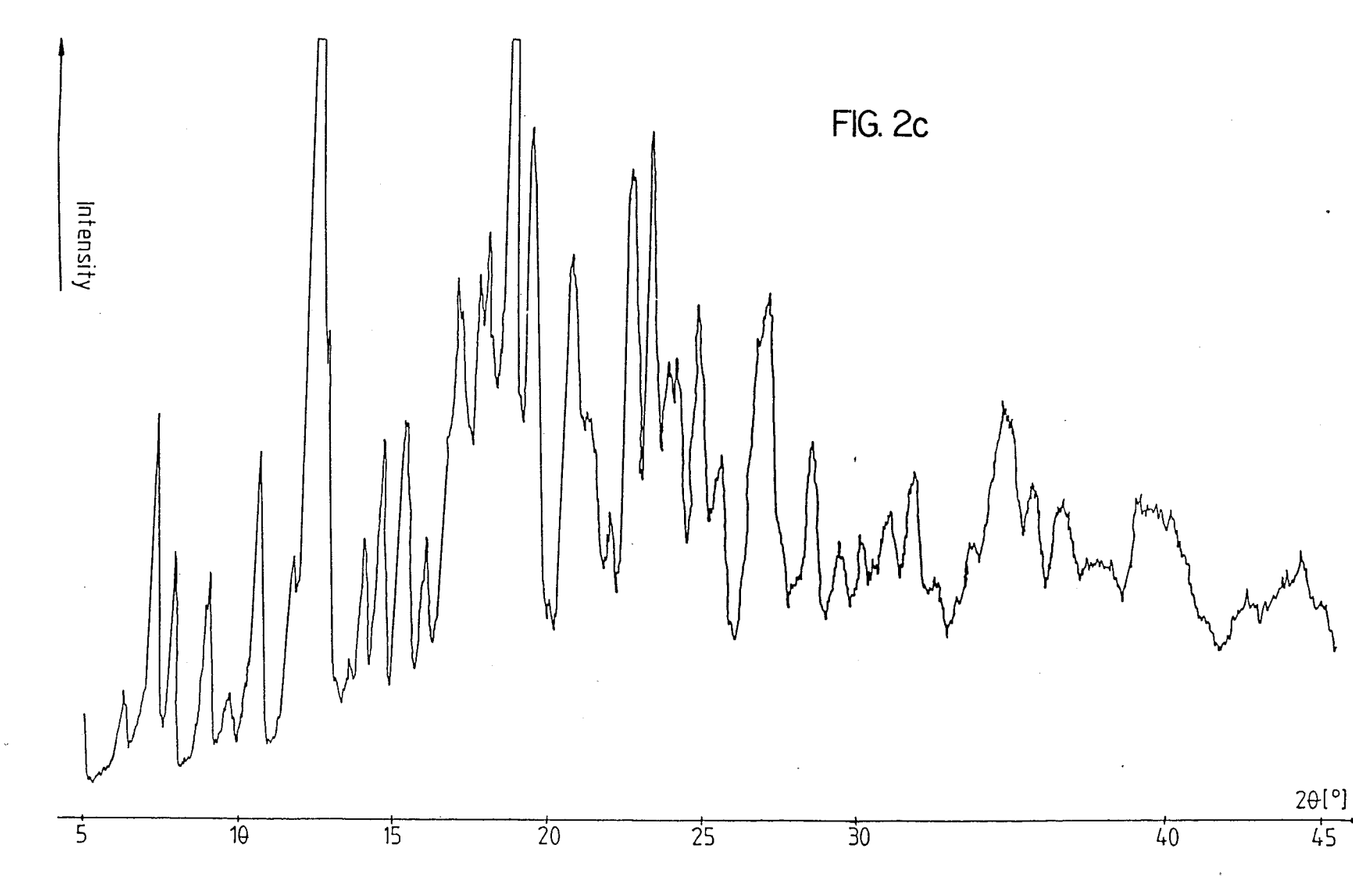
Figure 2D:
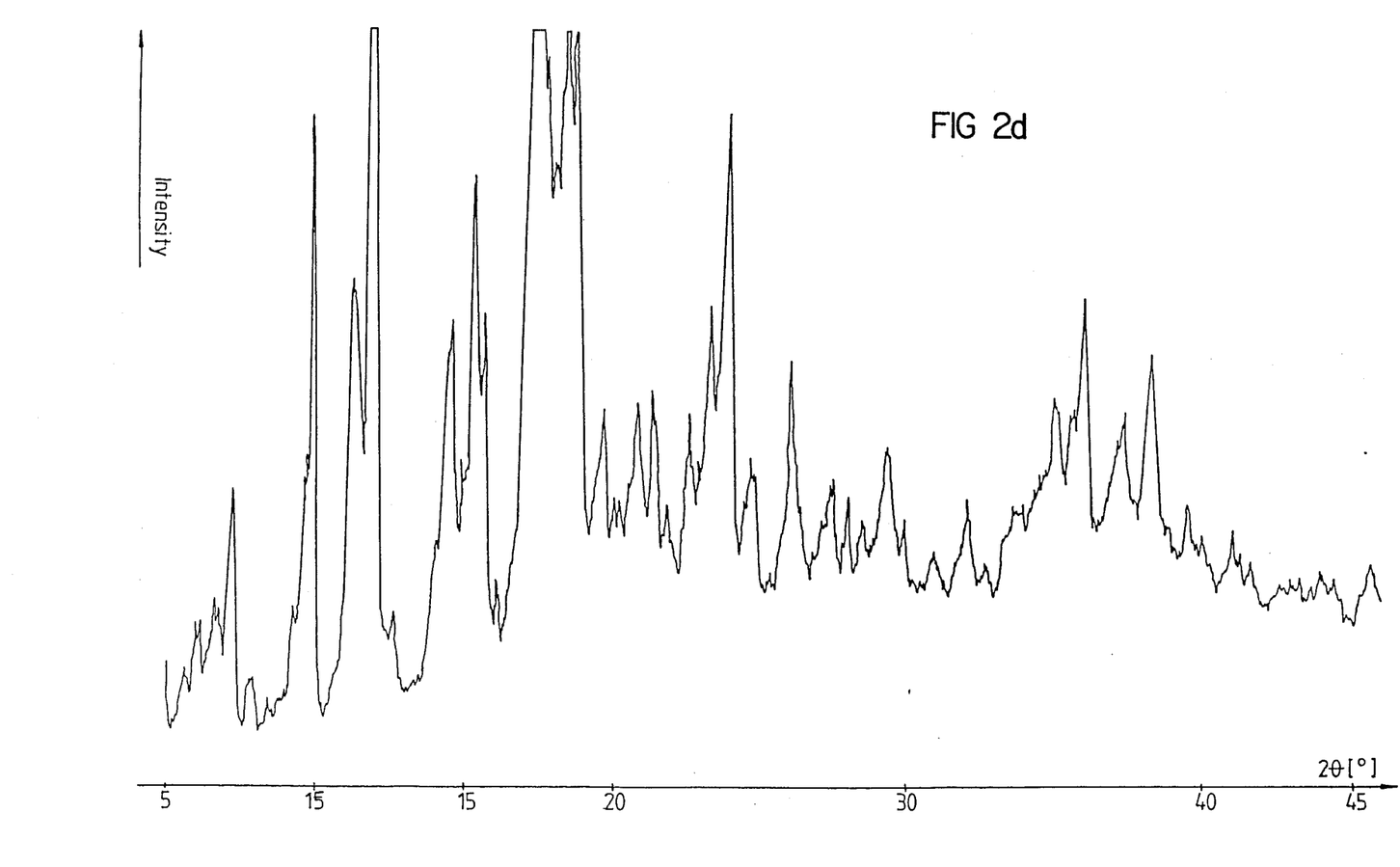

The differential scanning calorimetry (DSC) demonstrated that the product is in fact an inclusion complex. DSC scans of ibuproxam, beta-cyclodextrin, a physical mixture of both and the inclusion complex of ibuproxam with beta-cyclodextrin are shown in FIGS. 1 (a, b, c, d).

This thermoanalytical assay shows characteristic differences between the inclusion complex of ibuproxam with beta-cyclodextrin and the physical mixture of ibuproxam and beta-cyclodextrin. The DSC scan of beta-cyclodextrin shows a minimum below 100° C., corresponding to the elimination of water. The next change occurs above 270° C. where the decomposition of beta-cyclodextrin begins.

The DSC scan of ibuproxam alone shows the melting point at 123° C.

The DSC scan of the inclusion complex of ibuproxam with beta-cyclodextrin shows a characteristic minimum at 224° C.

Powder X-ray diffraction

The powder X-ray diffraction patterns of ibuproxam, beta-cyclodextrin, a physical mixture of ibuproxam and beta-cyclodextrin obtained by mechanical blending of both components in an equimolar ratio and of the inclusion complex as shown in FIGS. 2 (a, b, c, d) indicate that the spectrum of the inclusion complex differs from the spectra of both starting substances as well as from the spectrum of the physical mixture of the components. By way of illustration such diffraction maxima were selected which are intense and do not overlap in individual spectra.

| sample | 20 (°) |
|---|---|
| ibuproxam | 7.221, 7.803 |
| beta-cyclodextrin | 9.023, 10.710, 12.521 |
| inclusion complex | 11.852, 11.984 |
| physical mixture | 7.257, 7.826 (corresponds to the maximum for ibuproxam at 20: 7.221° and 7.803°) |
|  | 10.602, 12.436 (corresponds to the maximum for beta-cyclodextrin at 20: 10.710° and 12.521°) |
|  | There are no characteristic maxima for the inclusion complex at 20: (11.852°, 11.984°) in the spectrum. |

EXAMPLE 5

Dissolution rates of complexed and non-complexed ibuproxam

A prerequisite for a successful pharmacological activity of orally administered drugs is their solubility in digestive juices. A good solubility, however, does not necessarily ensure a good dissolution rate although the solubility is one of the factors that affect the dissolution rate. All factors affecting the dissolution rate also affect the absorption rate and hence the onset speed, the intensivity and the duration of the pharmacological activity.

In order to demonstrate the influence of the inclusion of ibuproxam into its inclusion complex with beta-cyclodextrin upon the dissolution rate, the comparative dissolution rates of ibuproxam, of its inclusion complex with beta-cyclodextrin and of the physical mixture of both components were determined by Paddle Method on Apparatus 2 according to USP XXI.

The test samples contained the equivalent of 400 mg ibuproxam. The inclusion complex of ibuproxam with beta-cyclodextrin contained 13.9% of ibuproxam.

The dissolution tests were performed in 0.027N HCl and 0.06N HCl (artificial gastric juice) and in artificial intestinal juice, pH 6.0, at the temperature of 37° C. The volume of the artificial biological fluids was 1000 ml. The stirring rate of the paddle mixer was 100 rpm. The quantities of the dissolved ibuproxam were determined spectrophotometrically.

TABLE 1

Apparatus 2 (USP XXI), 100 rpm
Medium: artificial gastric juice, pH 1.2 = 0.06 N HCL, 1000 ml
pH 1.6 = 0.027 N HCl, 1000 ml
artificial intestinal juice, pH 6.0, 1000 ml
Temperature: 37 ± 0.5° C.

|  |  | % of dissolved ibuproxam | | artificial intestinal juice |
|---|---|---|---|---|
|  |  | 0.06 N HCl | 0.027 N HCl |  |
| ibuproxam (400 mg) | 5 min | 21.8 | 21.4 | 10.2 |
|  | 15 min | 29.8 | 28.1 | 21.2 |
|  | 30 min | 37.4 | 33.3 | 27.7 |
|  | 45 min | 40.4 | 37.4 | 32.7 |
|  | 60 min | 41.7 | 43.1 | 33.3 |
| inclusion complex of ibuproxam with beta-cyclodextrin (equ. 400 mg) | 5 min | 92.7 | 92.8 | 91.1 |
|  | 15 min | 97.4 | 98.4 | 93.7 |
|  | 30 min | 101.9 | 101.7 | 95.7 |
|  | 45 min | 102.3 | 101.9 | 96.3 |
|  | 60 min | 102.0 | 101.9 | 98.2 |

Figure 3:
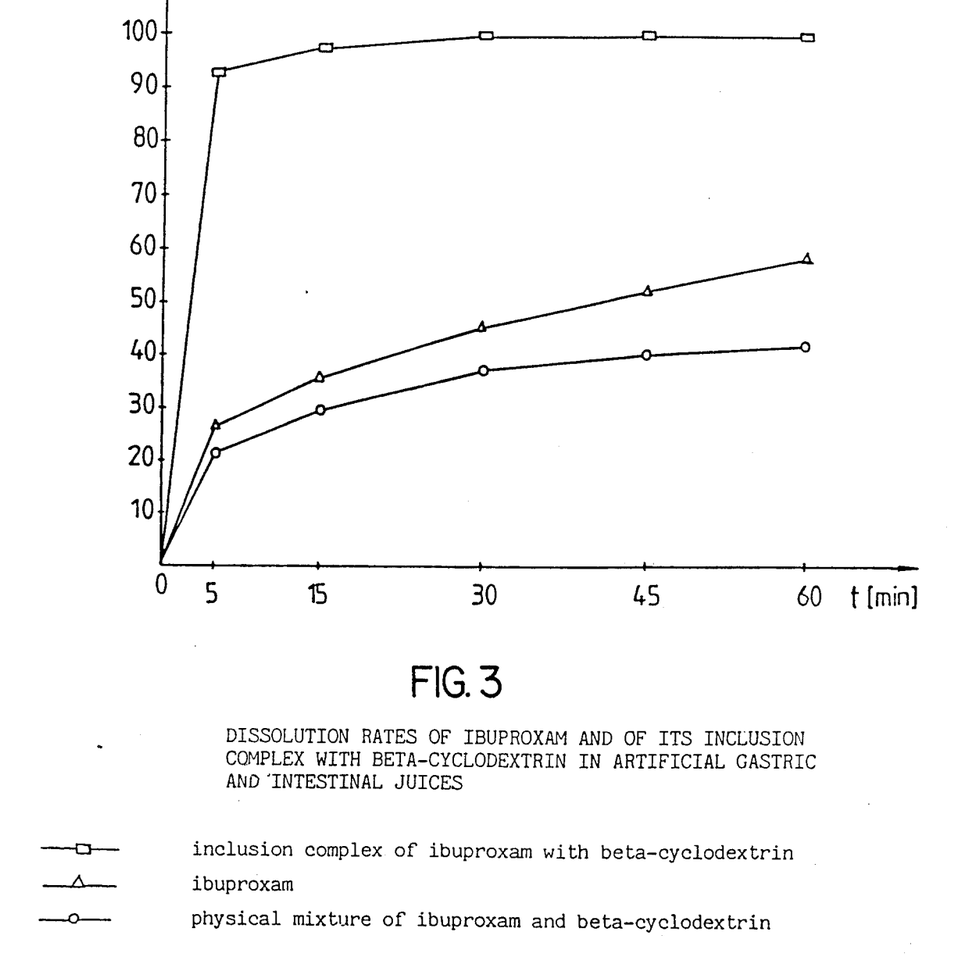

FIG. 3 shows the dissolution rates of ibuproxam and of its inclusion complex with beta-cyclodextrin in artificial gastric and intestinal juices. From the figures and from Table 1 it is evident that the dissolution rate of ibuproxam is considerably increased by complexing. After 5 min the portion of the dissolved ibuproxam in artificial gastric and intestinal juices is 21.8%, 21.4% and 10.2% resp., whereas for the complexed ibuproxam these values are 92.7%, 92.8% and 91.1% resp.

We think that the increase in the dissolution rate is due to the increase of the water-solubility, the decrease of the crystallinity and the increase of the wettability of the complexed ibuproxam.

EXAMPLE 6

Acute toxicity

In toxicological tests acute toxicities ($LD_{50}$) of ibuproxam and of its inclusion complex with beta-cyclodextrin were determined in female and male mice after oral and intraperitoneal administration. The doses are calculated with respect to the content of 13.9% of ibuproxam in the complex. The following Table 2 shows the results of testing.

TABLE 2

|  | Intraperitoneal application $LD_{50}$ mg/kg | |
|---|---|---|
|  | ♂ | ♀ |
| ibuproxam | 550 | 492.9 |
| inclusion complex of ibuproxam with beta-cyclodextrin | 979.6 | 960.20 |
|  | Oral application $LD_{50}$ mg/kg | |
|  | ♂ | ♀ |
| ibuproxam | 2369 | 1756 |
| inclusion complex of ibuproxam with beta-cyclodextrin | 2973 | 2660 |

From Table 2 it is evident that the inclusion complex of ibuproxam with beta-cyclodextrin is less toxic than ibuproxam alone.

EXAMPLE 7

In vitro tests

Effect of inclusion of ibuproxam in the inclusion complex with beta-cyclodextrin on dissolution and resorption rates under in vitro conditions The resorption tests were performed according to the Stricker method on a Sartorius Dissolution Model (Sartorius Dissolution Model, Instruction Manual, Sartorius Membranfilter, Göttingen 1972). The diffusion rates of ibuproxam through artificial lipid membranes at different pH values were determined. On the basis of the found diffusion rate constants ($k_d$) the in vitro resorption rate constants ($k_a$) were calculated.

TABLE 3

| In vitro diffusion rate constants ($k_d$) and resorption rate constants ($k_a$) for ibuproxam, allowing for the proportionality constant G | | | | |
|---|---|---|---|---|
| pH of the artificial gastro-intestinal juice | (a) $k_d$ (cm min$^{-1}$) | S.E. | (b) G (cm$^{-1}$) | $k_a$ (min$^{-1}$) |
| 1.2 | $1.41 \cdot 10^{-2}$ | $\pm 0.5 \cdot 10^{-3}$ | 4.3 | 0.060 |
| 3.0 | $1.43 \cdot 10^{-2}$ | $\pm 0.4 \cdot 10^{-3}$ |  |  |
| 6.0 | $1.40 \cdot 10^{-2}$ | $\pm 0.3 \cdot 10^{-3}$ | 10.0 | 0.138 |

(a)average of 4 tests
(b)experimental factor which varies for differents parts of the gastro-intestinal tract (human stomach and intestine resp.)

The quantities of the dissolved ($M_G$) and of the resorbed ($M_i$) active ingredient were determined using a Sartorius Dissolution Model SM 16751 (Sartorius Dissolution Model, Instruction Manual, Sartorius Membranfilter, Göttingen 1972).

Figure 4:
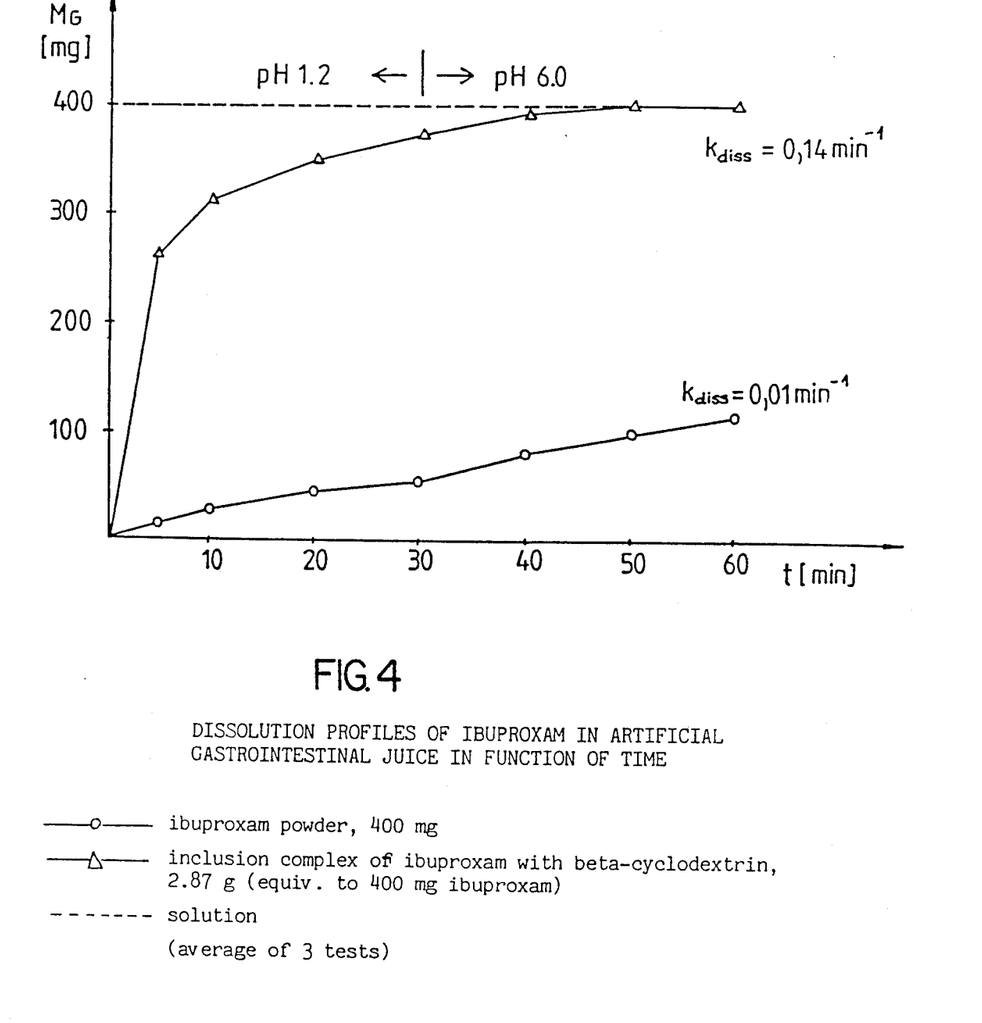

FIG. 4 shows the comparative dissolution profiles of non-complexed ibuproxam powder and of the inclusion complex of ibuproxam with beta-cyclodextrin resp. It is evident therefrom that the dissolution rate is significantly increased by complexing.

Figure 5:
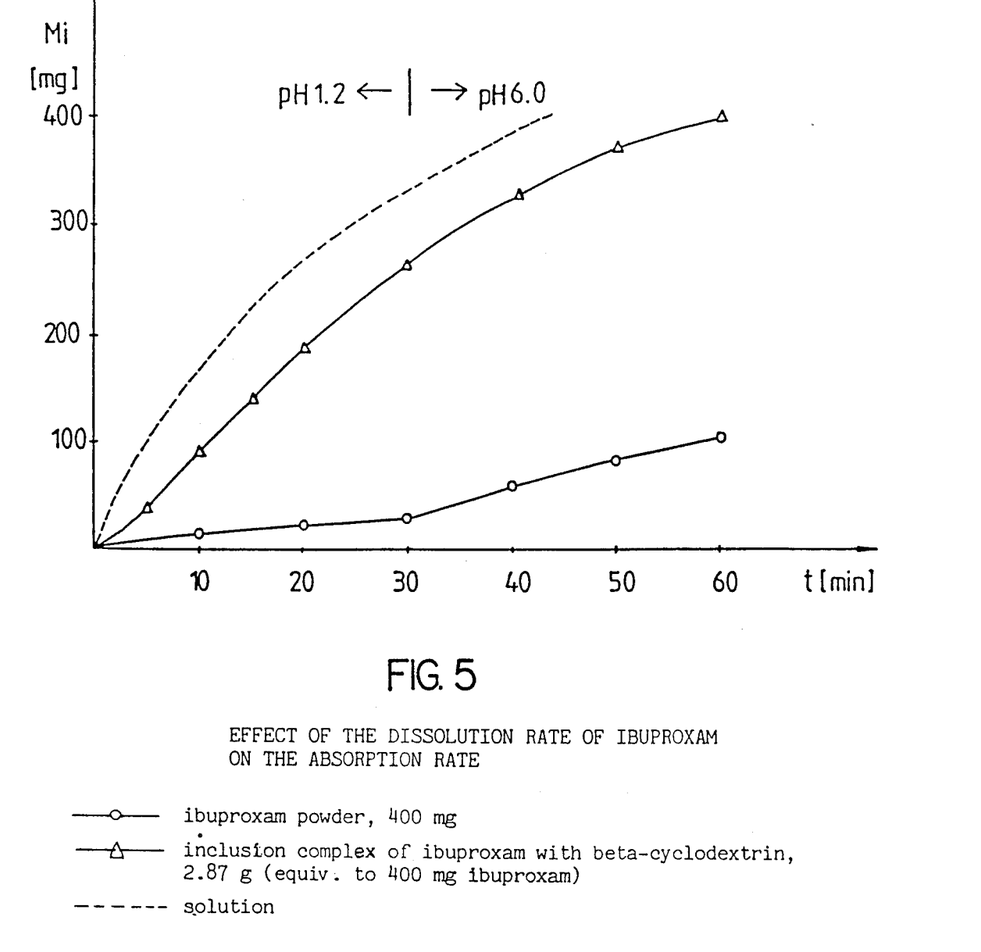
Figure 6:
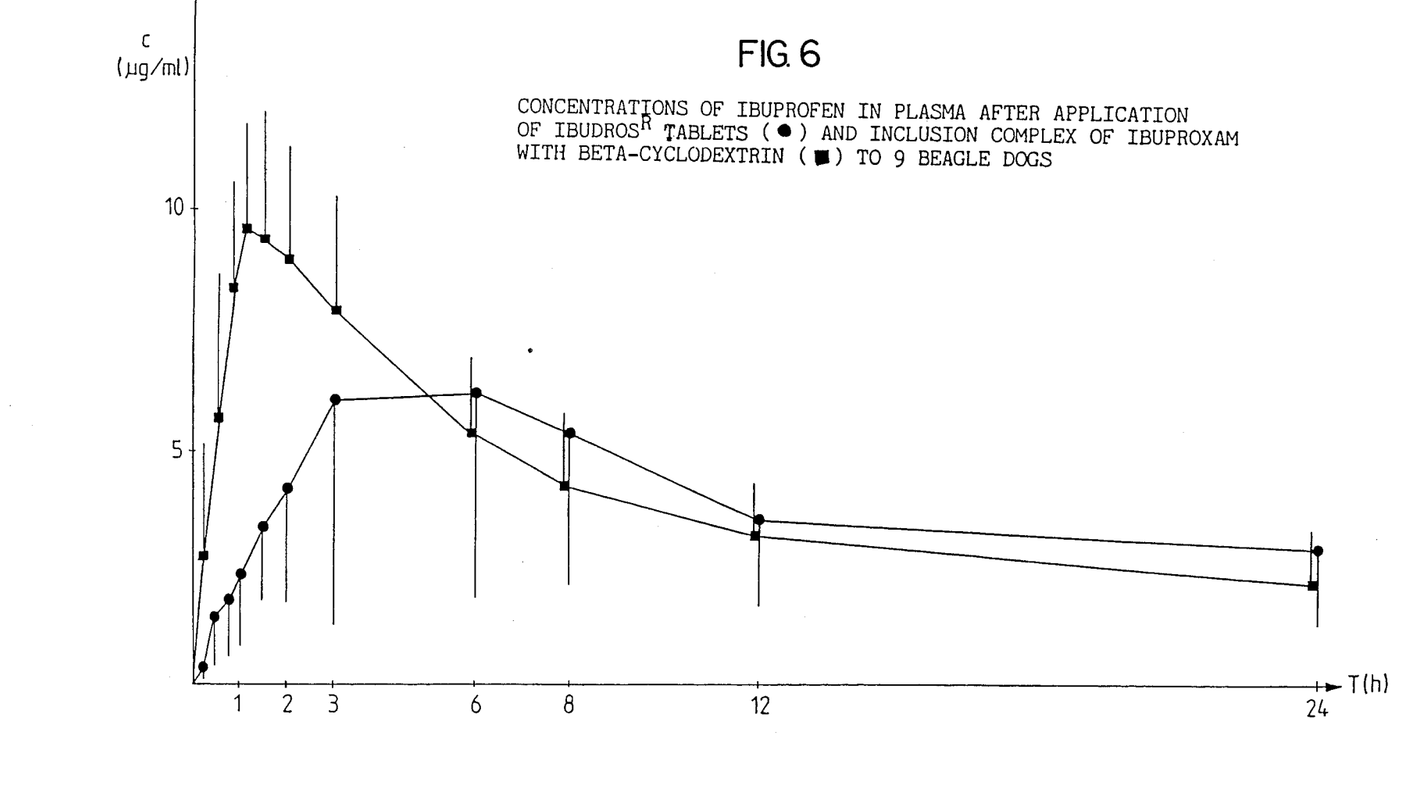

FIG. 5 shows the effect of the dissolution rate of ibuproxam on the resorption rate under in vitro conditions. In the cases when the active ingredient is poorly soluble in water ($k_d < k_a$) the dissolution rate is the determinative factor for the resorption step.

In vitro ibuproxam release from pharmaceutical forms

Determination of ibuproxam in test samples

Spectrophotometric determination: Filtered test solutions were suitably diluted with 0.027N hydrochloric acid and absorbancies were measured at a wavelength of about 222 nm against a standard solution of ibuproxam of known concentration in the same medium.

Dissolution test

Paddle Method, USP XXI (United States Pharmacopoeia Conv. 1243–1244/1985)
Apparatus 2: 100 rpm
Dissolution medium: 0.027 HCl, 1000 ml
Temperature 37±0.5° C.
Time: 15, 30, 60 min

TABLE 4

| Ibuproxam release from different pharmaceutical forms | | | |
|---|---|---|---|
|  | % dissolved within | | |
|  | 15 min | 30 min | 60 min |
| ibuproxam powder (400 mg) | 35.8 | 43.4 | 54.5 |
| inclusion complex of ibuproxam with beta-cyclodextrin (1.43 g; equiv. to 200 mg ibuproxam) | 98.9 | 100.2 | 100.2 |
| Ibudros ® tablets (400 mg) | 1.5 | 2.1 | 12.5 |

Ibudros ® is a trade name of the Italian firm Manetti H. Roberts.

The results represent a mean of 3 values.

The results in Table 4 show that the ibuproxam release from the complex is twice as high as from the non-complexed ibuproxam, i.e. the same action can be achieved by only half the dosage.

EXAMPLE 8

Comparison of the inclusion complex of ibuproxam with beta-cyclodextrin (IBX-CD) and of the commercial preparation Ibudros ® in beagle dogs Similarly to the dissolution rate, the amount of the active substance (ibuproxam) resorbed from the intestinal tract is also increased as a consequence of the complexing. Therefore the pharmacokinetic properties of the inclusion complex of ibuproxam with beta-cyclodextrin in capsules and of the commercial preparation Ibudros ® tablets were compared. The tests were performed in 9 beagle dogs. In a randomized cross-over trial 1 tablet of Ibudros ® (400 mg of ibuproxam) and 1 capsule containing 1.45 g of the inclusion complex of ibuproxam with beta-cyclodextrin (13.7%, i.e. 200 mg ibuproxam) resp. were administered to each dog. The dogs were left without food overnight and administered the preparations in the morning. Sequential samples of venous blood (5 ml) were collected immediately before the administration and 0.25, 0.5, 0.75, 1, 1.5, 2, 3, 6, 8, 12 and 24 hours after the administration. The samples were centrifugated for 15 minutes at 3000 rpm and the supernatant plasma samples were frozen until analyzed. The plasma concentrations were determined by the HPLC method. Since in plasma ibuproxam is immediately converted to its metabolite ibuprofen, only the concentrations of ibuprofen in the plasma were determined.

Pharmacokinetic estimations

After the administration of Ibudros ® tablets the pharmacokinetic parameters were calculated for 6 dogs according to the open single compartment model and for 3 dogs according to the open two-compartment model. After the administration of the complex the open single compartment model was used in 4 dogs and the open two-compartment model in 5 dogs.

The elimination constants ($k_{el}$) and the corresponding biological half-lives ($t_{\frac{1}{2}}el$) were calculated from the terminal linear part of the transformed lnC/t curve. The absorption constants ($k_a$) and the distribution constants ($\alpha$) were calculated according to the stripping method.

The areas under the plasma concentration-time curves (AUC) were calculated for the 24 hrs period according to the trapezoidal rule and then corrected to the infinite time according to the 1st order kinetics.

The maximum concentration ($C_{max}$) and the times necessary to reach these maximum concentrations ($t_{max}$) were estimated from the experimental data.

Student's t-test was used for the statistical data processing.

Results

Plasma concentration of ibuprofen after the administration of Ibudros ® tablets are shown in Table 6. Table 7 shows the plasma concentrations of ibuprofen after the administration of the inclusion complex of ibuproxam with beta-cyclodextrin. A graphical representation of the mean values and standard deviations for both preparations is shown in Diagram 1.

The maximum plasma concentrations ($C_{max}$) for Ibudros ® tablets are 7.49±4.4 µg/ml and for the inclusion complex of ibuproxam with beta-cyclodextrin they are 10.23±2.63 µg/ml. The difference is not statistically significant.

The times necessary to reach the maximum concentration ($t_{max}$) are 3.50±2.0 h for Ibudros ® tablets and 1.25±0.39 h for the inclusion complex of ibuproxam with beta-cyclodextrin. The difference is statistically significant at the 0.05 level.

The elimination constant ($k_{el}$) is 0.0383±0.0166 $h^{-1}$ for Ibudros ® tablets and 0.0538±0.0297 $h^{-1}$ for the inclusion complex of ibuproxam with beta-cyclodextrin. The difference is not statistically significant.

The biological half-lives for Ibudros ® tablets and for the inclusion complex of ibuproxam with beta-cyclodestrin are 21.61±9.86 h and 18.37±12.31 h resp. The difference is not statistically significant.

The absorption constants for Ibudros ® tablets and for the inclusion complex of ibuproxam with beta-cyclodextrin are 1.181±1.503 $h^{-1}$ and 4.938±2.927 $h^{-1}$ resp. The difference is statistically significant at the 0.05 level.

The corresponding absorption half-lives for Ibudros ® tablets and for the inclusion complex of ibuproxam with beta-cyclodextrin are 1.190±0.725 h and 0.208±0.151 h resp. The difference is statistically significant at the 0.05 level.

The areas under the plasma concentration-time curves for the 24 h period ($AUC^{0-24}$) for Ibudros ® tablets and for the inclusion complex of ibuproxam with beta-cyclodextrin are 96.528±51.727 µg.h/ml and 101.216±25.416 µg.h/ml resp. The difference is not statistically significant.

The relative bioavailability of the inclusion complex of ibuproxam with beta-cyclodextrin is 104.86% with respect to Ibudros ® tablets. Since it has to be taken into account that the dosage of the inclusion complex of ibuproxam with beta-cyclodextrin was only one half of dosage of ibuproxam in the Ibudros ® tablet, the real relative bioavailability of the inclusion complex of ibuproxam with beta-cyclodextrin is 209.71%.

The areas under the plasma concentration-time curves, corrected for infinity ($AUC^{0-\infty}$) for Ibudros ® tablets and for the inclusion complex of ibuproxam with beta-cyclodextrin are 182.619±93.922 µg.h/ml and 162.900±81.965 µg.h/ml resp. The difference is not significant. The relative bioavailability of the inclusion complex of ibuprocam with beta-cyclodextrin is 89.20% and—considering the dosage—178.40%.

Hence it can be concluded from the above results that the complexing strongly affects both the absorption rate and the relative bioavailability of ibuproxam.

All the pharmacokinetic parameters calculated for both preparations are listed in Table 8.

TABLE 6

Plasma concentrations of ibuprofen after administering Ibudros ® tablets (400 mg) to nine beagle dogs (µg/ml)

| animal time (h) | 261 | 263 | 287 | 215 | 255 | 298 | 297 | 202 | 162 | $\bar{X}$ | SD | RSD | Student's t-test | |
|---|---|---|---|---|---|---|---|---|---|---|---|---|---|---|
| 0.25 | 0.9 | 0.0 | 0.6 | 0.0 | 0.4 | 0.7 | 0.4 | 0.2 | 0.6 | 0.42 | 0.31 | 73.74 | 3.108 | (0.05) |
| 0.50 | 1.1 | 0.9 | 2.7 | 0.0 | 2.0 | 3.1 | 1.4 | 0.4 | 0.9 | 1.39 | 1.03 | 74.17 | 5.533 | (0.01) |
| 0.75 | 1.2 | 2.0 | 3.8 | 0.0 | 2.3 | 3.6 | 1.7 | 0.7 | 1.0 | 1.81 | 1.27 | 70.36 | 8.256 | (0.01) |
| 1.00 | 1.3 | 2.9 | 4.9 | 0.6 | 2.5 | 3.7 | 2.1 | 0.8 | 2.0 | 2.31 | 1.39 | 60.01 | 7.912 | (0.01) |
| 1.50 | 1.5 | 5.4 | 5.7 | 3.0 | 3.9 | 3.0 | 2.8 | 0.9 | 3.6 | 3.31 | 1.58 | 47.81 | 5.891 | (0.01) |
| 2.00 | 1.0 | 7.6 | 7.5 | 3.6 | 4.1 | 2.8 | 3.2 | 1.7 | 5.8 | 4.14 | 2.37 | 57.10 | 5.037 | (0.01) |
| 3.00 | 0.9 | 13.8 | 12.8 | 5.2 | 6.5 | 2.7 | 4.1 | 3.7 | 5.1 | 6.09 | 3.39 | 72.18 | 1.487 | (NS) |
| 6.00 | 0.8 | 13.0 | 8.2 | 8.6 | 11.5 | 2.2 | 6.0 | 2.9 | 3.0 | 6.24 | 4.34 | 69.44 | 0.610 | (NS) |
| 8.00 | 0.7 | 9.9 | 6.5 | 6.8 | 9.8 | 2.2 | 5.4 | 2.8 | 4.2 | 5.37 | 3.23 | 60.13 | 0.955 | (NS) |
| 12.0 | 0.7 | 6.6 | 3.5 | 5.1 | 5.6 | 2.2 | 3.6 | 1.8 | 3.2 | 3.59 | 1.90 | 53.08 | 0.409 | (NS) |
| 24.0 | 0.5 | 3.5 | 1.7 | 4.3 | 5.7 | 2.6 | 3.8 | 1.1 | 3.0 | 2.91 | 1.64 | 56.33 | 1.218 | (NS) |

$\bar{X}$ = average
SD = standard deviation
RSD = relative standard deviation
NS = nonsignificant

TABLE 7

Plasma concentrations of ibuprofen after administering the complex of ibuproxam with beta-cyclodextrin (200 mg ibuproxam) to nine beagle dogs (μg/ml)

| animal time (h) | 261 | 263 | 287 | 215 | 255 | 298 | 297 | 202 | 162 | $\bar{X}$ | SD | RSD |
|---|---|---|---|---|---|---|---|---|---|---|---|---|
| 0.25 | 4.1 | 0.0 | 0.3 | 0.0 | 3.5 | 3.5 | 6.8 | 4.8 | 2.1 | 2.9 | 2.37 | 85.13 |
| 0.50 | 4.8 | 4.5 | 10.9 | 0.8 | 7.9 | 6.0 | 8.5 | 3.1 | 4.7 | 5.9 | 3.04 | 53.39 |
| 0.75 | 5.6 | 8.5 | 11.7 | 7.9 | 8.6 | 6.1 | 9.3 | 11.7 | 6.6 | 8.4 | 2.21 | 26.23 |
| 1.00 | 7.9 | 11.3 | 12.1 | 12.5 | 9.1 | 6.6 | 8.5 | 11.8 | 7.1 | 9.6 | 2.29 | 23.72 |
| 1.50 | 9.3 | 11.0 | 10.5 | 14.7 | 8.7 | 6.1 | 7.8 | 12.1 | 6.6 | 9.6 | 2.75 | 28.49 |
| 2.00 | 7.5 | 11.8 | 10.0 | 12.6 | 8.1 | 6.3 | 7.3 | 11.2 | 6.5 | 9.3 | 2.40 | 26.58 |
| 3.00 | 6.2 | 11.4 | 9.0 | 11.8 | 7.3 | 6.6 | 4.1 | 10.2 | 5.3 | 7.9 | 2.74 | 34.29 |
| 6.00 | 4.2 | 6.9 | 5.9 | 6.3 | 5.5 | 4.9 | 3.4 | 8.1 | 3.6 | 5.2 | 1.56 | 28.82 |
| 8.00 | 3.9 | 5.7 | 5.3 | 2.2 | 4.2 | 4.8 | 2.9 | 6.5 | 2.7 | 4.4 | 1.46 | 34.47 |
| 12.0 | 2.6 | 4.4 | 4.1 | 2.1 | 3.6 | 4.2 | 2.2 | 4.5 | 2.0 | 3.0 | 1.06 | 32.18 |
| 24.0 | 2.1 | 3.6 | 2.9 | 2.8 | 2.3 | 2.9 | 0.8 | 1.2 | 1.0 | 2.8 | 0.98 | 45.09 |

$\bar{X}$ = average
SD = standard deviation
RSD = relative standard deviation

TABLE 8

Pharmaco-kinetic parameters of ibuprofen after administering Ibudros ® tablets (400 g) and the inclusion complex of ibuproxam with beta-cyclodextrin to 9 beagle dogs

| parameter | inclusion complex of ibuproxam with beta-cyclodextrin | IBUDROS ®R | |
|---|---|---|---|
| $C_{max}$ (μg/ml) | 10.23 ± 2.63 | 7.49 ± 4.40 | NS |
| $t_{max}$ (h) | 1.25 ± 0.39 | 3.5 ± 2.0 | P < 0.05 |
| $k_{el}$ (h$^{-1}$) | 0.054 ± 0.029 | 0.038 ± 0.017 | NS |
| $t_{\frac{1}{2} el}$ (h) | 18.37 ± 12.31 | 21.61 ± 9.86 | NS |
| $k_a$ (h$^{-1}$) | 4.938 ± 2.927 | 1.181 ± 1.503 | p < 0.05 |
| $t_{\frac{1}{2} a}$ (h) | 0.208 ± 0.151 | 1.190 ± 0.725 | p < 0.05 |
| $AUC^{0-24}$ (μg · h/ml) | 101.216 ± 25.416 | 96.528 ± 51.727 | NS |
| $AUC^{0-\infty}$ (μg · h/ml) | 162.900 ± 81.965 | 182.619 ± 93.922 | NS |
| $\alpha$ (h$^{-1}$) | 0.344 ± 0.020 | 0.865 ± 0.942 | |

On the basis of the performed tests the following essential physico-chemical and pharmaceutical characteristics of the inclusion complex of ibuproxam with beta-cyclodextrin with reference to noncomplexed ibuproxam can be summarized as follows:

Owing to the poor solubility of ibuproxam in an aqueous medium, there is obtained a considerable improvement in aqueous solubility by complexing ibuproxam into the structure of the cyclodextrin molecule, whereat a new inclusion complex in the form of white powder is formed.

The inclusion complex of ibuproxam with beta-cyclodextrin is less toxic than ibuproxam alone.

The pH of the biological fluids does not affect the dissolution rate of ibuproxam ($k_{diss}=0.01$ min$^{-1}$).

the complexing of ibuproxam with beta-cyclodextrin significantly increases the dissolution rate ($k_{diss}=0.14$ min$^{-1}$).

The complex has a considerably greater absorption constant than ibuproxam in the commercial preparation Ibudros ® tablets.

The relative bioavailability of the complex calculated on the dosage basis is about 100% greater than that of the preparation Ibudros ® tablets.

Statistically significant differences are also observed in respect of the time needed to reach the maximum plasma concentration as well as in respect of the average plasma concentrations at 6 out of 11 observation times (without considering the difference in the dose).

The same activity is achieved with half the dose of ibuproxam.

EXAMPLE 9

Capsules of the following composition are prepared:

| | |
|---|---|
| inclusion complex of ibuproxam with beta-cyclodextrin (ibuproxam content 200 mg) | 1450 mg |
| talc | 8.8 mg |
| Aerosil 200 | 1.2 mg |
| | 1460.0 mg |

The composition is filled into hard gelatin capsules.

What is claimed is:

1. An inclusion complex of ibuproxam with beta-cyclodextrin.

2. An inclusion complex according to claim 1, characterized in that the molar ratio of ibuproxam and beta-cyclodextrin is 1:1.

3. An inclusion complex according to claim 1, characterized in that the content of ibuproxam in the complex is 13% to 15% by weight.

4. A pharmaceutical preparation having analgesic, antipyretic and antiinflammatory activity, comprising a therapeutically effective amount of the inclusion complex of ibuproxam with beta-cyclodextrin as the active ingredient together with pharmaceutically acceptable carriers.

* * * * *